United States Patent
Jackson et al.

(10) Patent No.: US 11,751,583 B2
(45) Date of Patent: Sep. 12, 2023

(54) PET FOOD COMPOSITION AND METHOD OF MAKING PET FOOD COMPOSITION COMPRISING ENHANCED LEVELS OF RESISTANT STARCH

(71) Applicant: Hill's Pet Nutrition, Inc., Topeka, KS (US)

(72) Inventors: Matthew Jackson, Topeka, KS (US); Christopher Waldy, Maple Hill, KS (US); Dennis Jewell, Lawrence, KS (US); Eden Ephraim, Lawrence, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 482 days.

(21) Appl. No.: 16/769,465

(22) PCT Filed: Dec. 5, 2017

(86) PCT No.: PCT/US2017/064677
§ 371 (c)(1),
(2) Date: Jun. 3, 2020

(87) PCT Pub. No.: WO2019/112562
PCT Pub. Date: Jun. 13, 2019

(65) Prior Publication Data
US 2021/0186056 A1 Jun. 24, 2021

(51) Int. Cl.
| | | |
|---|---|---|
| *A23K 20/163* | (2016.01) |
| *A23K 40/25* | (2016.01) |
| *A23K 50/40* | (2016.01) |
| *A23K 10/30* | (2016.01) |
| *A61K 9/00* | (2006.01) |
| *A61K 31/718* | (2006.01) |

(52) U.S. Cl.
CPC ............ *A23K 20/163* (2016.05); *A23K 10/30* (2016.05); *A23K 40/25* (2016.05); *A23K 50/40* (2016.05); *A61K 9/0056* (2013.01); *A61K 31/718* (2013.01)

(58) Field of Classification Search
CPC ...... A23K 10/30; A23K 40/25; A23K 20/163; A23K 50/40; A61K 9/0056; A61K 31/718; Y02P 60/87
USPC .......................................................... 514/60
See application file for complete search history.

(56) References Cited

U.S. PATENT DOCUMENTS

| | | |
|---|---|---|
| 5,480,669 A | 1/1996 | Zallie et al. |
| 6,303,174 B1 | 10/2001 | McNaught et al. |
| 7,252,836 B2 | 8/2007 | Brown et al. |
| 7,648,723 B2 | 1/2010 | Zimeri et al. |
| 8,613,971 B2 | 12/2013 | Finocchiaro et al. |
| 8,993,039 B2 | 3/2015 | Harrison et al. |
| 2007/0092620 A1* | 4/2007 | Zimeri ..................... A23L 7/17 426/549 |
| 2016/0082058 A1 | 3/2016 | Pan |
| 2016/0289653 A1 | 10/2016 | Gebert et al. |

FOREIGN PATENT DOCUMENTS

| | | |
|---|---|---|
| CN | 103907817 A * | 7/2014 |
| JP | 2013135690 A | 7/2013 |
| JP | 2017534576 A | 11/2017 |
| WO | 2016/130981 | 8/2016 |

OTHER PUBLICATIONS

Lin; CN 103907817 A; Jul. 9, 2014 (Machine-English Translation).*
Spears et al. (Journal of AOAC International vol. 87, No. 3, 2004, 787-791).*
International Search Report and the Written Opinion of the International Searching Authority issued in International Application PCT/US2017/064677 dated Jul. 5, 2018.
Kleessen et al., 1997, "Feeding Resistant Starch Affects Fecal And Cecal Microflora Ans Short-Chain Fatty Acids In Rats," Journal Of Animal Science 75(9):2453-2462.
Panasevich et al., 2015, "Modulation of the faecal microbiome of healthy adult dogs by inclusion of potato fibre in the diet," British Journal of Nutrition 113(01):125-133.
Peixoto et al., 2017, "Effect of resistant starch on the intestinal health of old dogs: fermentation products and histological features of the intestinal mucosa," Journal of Animal Physiology And Animal Nutrition 102(1):e111-e121.

* cited by examiner

*Primary Examiner* — Layla D Berry (57) ABSTRACT

Disclosed herein is a pet food composition and methods of making a pet food composition using an extrusion process, wherein the resultant pet food composition comprises an enhanced level of resistant starch. The pet food compositions disclosed herein may increase the proportions of beneficial gastrointestinal bacteria, such as *Lactobacillus* and *Bifidobacterium*, while decreasing deleterious bacteria such as *Megamonas*. The improved microbial environment resulting from the pet food compositions disclosed herein having an enhanced level of resistant starch may lead to both improved gastrointestinal and psychobiotic health for the animal consuming the pet food composition.

14 Claims, 3 Drawing Sheets

PET FOOD COMPOSITION AND METHOD OF MAKING PET FOOD COMPOSITION COMPRISING ENHANCED LEVELS OF RESISTANT STARCH

BACKGROUND

Pet food compositions, such as dog and cat food compositions, may provide health and nutritional benefits to the companion animals that consume them. Frequently, pet food compositions are formed by an extrusion process, in which the raw material ingredients are extruded in an extrusion device under varying conditions of heat and pressure to yield the desired form. During the extrusion process, the raw material ingredients are typically subjected to high shear mixing forces, which result in a break-down of the starch in the raw materials. As the starch breaks down, it becomes more readily digestible by the consuming animal.

If the starch is not absorbed or digested in the stomach or small intestine, it is known as a resistant starch. Resistant starches then enter the lower gastrointestinal tract of animals where they may be digested by microbiota that reside in the large intestine. Resistant starches have several health benefits, such as maintaining or improving the proportion of beneficial bacteria in relation to deleterious bacteria in the gastrointestinal tract of animals. Accordingly, a pet food composition comprising an enhanced level of resistant starches and a method of making a pet food composition comprising an enhanced level of resistant starches would be beneficial to companion animals and their caregivers.

Furthermore, one major feature of aging in animals is dysbiosis, a reduction in the proportion of beneficial bacteria and an increase in deleterious bacteria in the gastrointestinal tract. This bacterial imbalance can cause the accumulation of toxic microbial metabolites in the animal's body. This, in turn, can lead to inflammation, oxidative stress, and various diseases. Accordingly, a pet food composition that maintains or improves the proportion of beneficial bacteria in relation to deleterious bacteria in the gastrointestinal tract of animals and a method of maintaining or improving the proportion of beneficial bacteria in relation to deleterious bacteria would be advantageous to animals, such as aging or senior animals.

BRIEF SUMMARY

Further disclosed herein are extruded pet food compositions comprising resistant starch in an amount of at least about 7%, such as about 7% to about 30%, at least about 10%, about 7% to about 20%, about 9% to about 13%, or about 20% to about 30%, by weight based on the total weight of the extruded pet food composition. In certain embodiments, a source of the resistant starch in the extruded pet food composition is at least one of corn, such as whole corn, and rice, such as brewer's rice. In certain other embodiments, the sole source of resistant starch in the extruded pet food composition is at least one of corn, such as whole corn, and rice, such as brewer's rice.

In certain embodiments disclosed herein, the extruded pet food composition may be in the form of a kibble, and in certain embodiments the extruded pet food composition may be in the form of a treat or snack. According to certain embodiments, the extruded pet food composition may be a dog food.

Also disclosed herein is a pet food composition made by a method comprising providing pet food raw materials for extrusion and extruding said pet food raw materials using an extrusion device, wherein a sum of the specific mechanical energy and the specific thermal energy of the extrusion device is less than about 60 W·h/kg, wherein the ratio of specific mechanical energy to specific thermal energy is less than 0.5, and wherein the extruded pet food composition comprises resistant starch in an amount of at least about 7% by weight based on the total weight of the pet food composition. In certain embodiments disclosed herein, a pet food composition made by the method disclosed herein comprises resistant starch in an amount ranging from about 7% to about 30%, or at least about 10%, or, in certain embodiments, ranging from about 7% to about 20%, such as from about 9% to about 13%, by weight based on the total weight of the pet food composition.

In certain embodiments, the pet food composition made by the methods disclosed herein may be in the form of a kibble, and in certain embodiments, may be in the form of a treat or snack. According to certain embodiments, the pet food compositions made by the methods disclosed herein may be a dog food.

Also disclosed herein is a pet food composition made by a method comprising providing pet food raw materials for extrusion and extruding the pet food raw materials using an extrusion device, wherein a specific mechanical energy of the extrusion device is less than about 25 W·h/kg, wherein the extruded pet food composition comprises resistant, starch in an amount of at least about 7% by weight based on the total weight of the pet food composition, and wherein the amount of at least, one of N6-carboxy 3-methyllysine, N6-carboxy 3-ethyl lysine, or pyrraline decreases in an animal who consumes the pet food composition. According to certain embodiments of the pet food composition made by the method disclosed herein, the amount of carnosine increases in an animal who consumes the pet food compositions, and, in certain embodiments, the levels of dopamine sulfate increase in an animal who consumes the pet food composition. According to certain embodiments of the pet food composition made by the method disclosed herein, the amount of 3-methyl catechol sulfate decreases in an animal who consumes the pet food composition.

Further disclosed herein is a method of increasing the proportion of at least one of *Lactobacillus* and *Bifidobacterium* in the gastrointestinal tract of an animal comprising administering a pet food composition to the animal, wherein the pet food composition comprises resistant starch in an amount of at least about 7%, such as about 7% to about 30%, at least about 10%, about 9% to about 13%, or about 7% to about 20%, by weight based on the total weight of the pet food composition. In certain embodiments, the pet food composition is made by the method comprising providing pet food raw materials for extrusion; and extruding said pet food raw materials using an extrusion device; wherein the total specific mechanical energy of the extrusion device is less than 25 W·h/kg and wherein the extruded pet food composition comprises resistant starch in an amount of at least about 7% by weight based on the total weight of the pet food composition; and wherein the animal consumes at least about 2.5 g of the resistant starch per kg of animal per day.

In certain embodiments, the method of increasing the proportion of at least one of *Lactobacillus* and *Bifidobacterium* further comprises decreasing the proportion of *Megamonas* in the gastrointestinal tract of the animal. In certain embodiments the animal is a senior animal, and in certain embodiments, the animal is a dog.

Also disclosed herein is a method of making a pet food composition comprising providing pet food raw materials for extrusion and extruding the pet food raw materials using an extrusion device, wherein a specific mechanical energy of the extrusion device is less than about 25 W·h/kg, and wherein the extruded pet food composition comprises resistant starch in an amount of at least about 7% by weight based on the total weight of the pet food composition.

According to certain embodiments of the methods disclosed herein, the amount of resistant starch ranges from about 9% to about 13% by weight based on the total weight of the pet food composition. In certain disclosed embodiments, a specific thermal energy of the extrusion device is greater than the specific mechanical energy of the extrusion device. In certain embodiments, the specific thermal energy of the extrusion device is about four times greater than the specific mechanical energy of the extrusion device.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiments is merely exemplary in nature and is in no way intended to limit the invention, its application, or uses.

Throughout the specification and claims, the following terms take the meanings explicitly associated herein, unless the context clearly dictates otherwise. The phrases "in some embodiments" and "in an embodiment" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, ail the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material. Unless otherwise specified, all component or composition amounts are in reference to the active amount of that component or composition, and exclude impurities or by-products, which may be present in commercially available sources.

All references cited herein are hereby incorporated by reference in their entireties. In the event of a conflict in a definition in the present disclosure and that of a cited reference, the present disclosure controls.

Disclosed herein are pet food compositions and methods for making pet food compositions comprising an enhanced amount of resistant starch. Further disclosed herein are methods for maintaining the gastrointestinal health of a companion animal, such as dog, by feeding the companion animal a pet food composition as disclosed herein. The compositions and methods disclosed herein are based, in part, on the discovery that administration of compositions comprising enhanced levels of resistant starch can improve the gastrointestinal health of a mammal, such as a companion animal. Companion animals include, for example, dogs, cats, rabbits, and horses.

The term "resistant starch" as used herein refers to starches and products of starch digestion that are not absorbed in the stomach or small intestine of mammals, but rather enter into the large intestine for digestion. Once in the large intestine, resistant starches may be fermented by microflora that is either resident naturally or introduced via diet, such as in the form of probiotics. Resistant starches may be categorized into at least five different groups, ranging from RSI to RSV. The categories of resistant starches include: (1) physically inaccessible starches (RSI), which include, for example, intact or partly milled grains and seeds, such as intact whole grains; (2) resistant native starches (RSII), which include, for example, raw potato, green banana, certain legumes, and high amylose maize; (3) retrograded starches (RSIII), which include, for example, cooked and cooled starchy foods, such as recrystallized maize or tapioca starch; (4) chemically modified starches (RSIV), which include, for example, starch ethers and esters cross-bonded starches, such as sodium trimetaphosphate (STMP)/sodiumpolyphosphate (STPP) cross-linked wheat starch, and (5) starch-lipid inclusion complexes (RSV), which include, for example, cooked, gelled, extruded starch in the presence of lipids, including polar lipids.

Resistant starches encompass all resistant starches including those derived from native and non-native sources. The resistant starches in the compositions disclosed herein may originate from a variety of different starch sources. For example, in certain embodiments the resistant starches may originate from at least one of corn, such as whole core, rice, such as brewer's rice; wheat; barley; soy; and oats and flours thereof. In certain embodiments disclosed herein, the sole source of the resistant starch for the compositions disclosed herein may be at least one corn, such as whole corn, and rice, such as brewer's rice.s As resistant starches are not digestible by the stomach or small intestine, they pass through an animal into the large intestine of the gastrointestinal tract, where the resistant starch may be fermented or digested by various microbiota species. The community of bacteria resident in the gastrointestinal tract comprises beneficial, deleterious, and inconsequential bacterial types or species. Whether a particular member of the digestive tract flora is beneficial, deleterious, or inconsequential to the health of the animal in particular circumstances can depend on a number of factors. Examples of beneficial members of the digestive tract flora include bifidobacteria, species of the genus *Bifidobacterium*, and lactic acid bacteria, species of the genus *Lactobacillus*. Deleterious bacteria include pathogenic bacteria, such as *Megamonas, Clostridium, Desulfovibrio, Helicobacter*, and pathogenic forms of *Escherichia coli*. Gastrointestinal health typically depends on the maintenance of an appropriate balance of beneficial and deleterious bacteria. Accordingly, an increase in the population of beneficial bacteria and/or a decrease in the population of deleterious bacteria can be associated with an improvement in gastrointestinal health.

Disclosed herein is a pet food composition comprising enhanced levels of resistant starch, such as a pet food composition comprising resistant starch in an amount of at least about 7% by weight based on the total weight of the pet food composition. In certain embodiments, the pet food composition disclosed herein may comprise, for example, at least about 9% resistant starch, at least about 10% resistant starch, at least about 15% resistant starch, at least about 20% resistant starch, at least about 25% resistant starch, or at least about 30% resistant starch, by weight based on the total weight of the pet food composition. In certain embodiments, the pet food composition disclosed herein may comprise a range of from about 7% to about 30%, such as from about 7% to about 20% or about 9% to about 13% resistant starch, by weight based on the total weight of the pet food composition.

The enhanced levels of resistant starch may lead to an increase in beneficial gastrointestinal tract bacteria in the large intestine and improved levels of metabolites in animals, such as age-related metabolites in senior animals. As used herein, the term "senior animals" refers to animals that are elderly, which may depend on the breed and species of animal. For example, for certain canines, senior may be defined as at least about 7 years old. The pet food compositions disclosed herein may induce an increase in the gastrointestinal tract proportions of the bacterial genera *Bifidobacterium* and *Lactobacillus* in animals, such as dogs, while decreasing the relative abundance of *Megamonas*, a genus consisting largely of disease causing bacteria. Further disclosed herein is a method of increasing the proportion of at least one of *Lactobacillus* and *Bifidobacterium* in the gastrointestinal tract of an animal comprising feeding the animal a pet food composition as disclosed herein comprising at least about 2.5 g of resistant starch per kg of animal per day. In certain embodiments, disclosed herein is a method of decreasing the proportion of *Megamonas* in the gastrointestinal tract of an animal comprising feeding the animal a pet food composition as disclosed herein comprising at least about 2.5 g of resistant starch per kg of animal per day.

This shift in the gastrointestinal tract microbiota may be accompanied by improved levels of metabolites associated with age-related health problems. These include, for example, a decline in Advanced Glycation End products (AGEs), such as pyrraline, N6-carboxymethyllysine, and N6-carboxyethyllysine, and the uremic toxin 3-methyl catechol sulfate. Moreover, the shift in gastrointestinal tract microbiota may further be accompanied by higher levels of dopamine sulfate in the blood of animals, such as senior dogs.

AGEs are a complex group of compounds derived from the non-enzymatic glycation of proteins, lipids, and nucleic acids in the body or in exogenous supplies such as food. AGEs cause inflammation and oxidative stress and are implicated in the pathogenesis of several chronic degenerative diseases of aging such as cardiovascular diseases, diabetic complications, renal failure, and cancer. In certain embodiments, the pet food compositions disclosed herein decrease the amounts of at least one of pyrraline, N6-carboxymethylline, and N6-carboxyethyllysine in an animal who consumes the pet food composition. In certain embodiments, the amounts of the at least one of pyrraline, N6-carboxymethylline, and N6-carboxyethyllysine may be measured in the feces of the animal and in certain embodiments it may be measured in the blood of the animal, such as in the serum. Accordingly, disclosed herein is a method of reducing the amount of at least one of pyrraline, N6-carboxymethylline, and N6-carboxyethyllysine in an animal comprising feeding the animal a pet food composition as disclosed herein, wherein the pet food composition fed to the animal comprises at least about 2.5 g of resistant starch per kg of animal per day. Further disclosed herein are methods of ameliorating chronic degenerative diseases, such as those caused, at least in part, by AGEs, in an animal in need thereof comprising feeding the animal an effective amount of a pet food composition as disclosed herein.

Additionally, levels of uremic toxins are reduced in animals consuming the pet food compositions disclosed herein. Uremic toxins are among the major toxic metabolites that lead to various diseases in aging. Although the majority of the uremic toxins originate endogenously from the host metabolism, some originate from fermentation of proteins in the colon by proteolytic bacteria. Products of the putrefaction process are absorbed and converted to toxic derivatives, which can burden kidney function. One example of such metabolites is 3-methyl catechol sulfate. In certain embodiments, the pet food compositions disclosed herein decrease the amount of 3-methyl catechol sulfate in an animal that consumes the pet food composition. In certain embodiments, the amounts of the 3-methyl catechol sulfate may be measured in the feces of the animal and in certain embodiments it may be measured in the blood of the animal, such as in the serum. Further disclosed herein are methods of ameliorating kidney disease, such as kidney disease caused at least in part by uremic toxins, in an animal in need thereof comprising feeding the animal an effective amount of a pet food composition as disclosed herein.

One of the organ systems most impacted by exposure to dietary AGE is the gastrointestinal tract, due to proximity and exposed surface area. In addition to preserving resistant starches to promote a more reduced global redox state, as indicated by lactate/pyruvate levels, the pet food compositions disclosed herein further preserve the bioactive dipeptide carnosine (ß-ALA-HIS). Carnosine has biological activity, acting as an AGE scavenger and decreasing negative health consequences of AGE exposure. In certain embodiments, the pet food compositions disclosed herein increase the amount of carnosine in an animal that consumes the pet food composition. In certain embodiments, the amounts of the carnosine may be measured in the feces of the animal and in certain embodiments it may be measured in the blood of the animal, such as in the serum.

Not only is gastrointestinal tract health important for an animal's physical well-being, for example in ameliorating chronic degenerative diseases attributed at least in part to AGEs and ameliorating kidney disease attributed at least in part to uremic toxins, but gastrointestinal health is also important to an animal's mental well-being. Recent insights from the gut-brain axis cross-talk have shown that changes in the gastrointestinal tract microbiota can either promote or reduce a healthy mental state. It has been shown that, in humans, the level of circulating dopamine sulfate correlates with that of dopamine. (Claustre et al., *Conjugation and deamination of circulating dopamine: relationship between sulfated and free dopamine in man*, J. AUTONOMIC NERVOUS SYS. 29(2): 175-181 (1990)). Dopamine is a key neurotransmitter for cognition and is known to decline with age, leading to impaired cognitive function and motor skills.

Certain foods and ingredients are known to increase the production of circulating dopamine and dopamine sulfate. As disclosed herein, senior dogs who consume the pet food compositions disclosed herein exhibit an increase in their dopamine sulfate levels in their blood, this increase in dopamine sulfate levels may imply the pet food compositions disclosed herein have a positive psychobiotic effect. Psychobiotics are substances that exert a microbiome-mediated production of metabolites, which have a psychological effect. (Sarkar et al., *Psychobiotics and the manipulation of bacteria gut-brain signals*, TRENDS IN NEUROSCIENCE 39(11): 763-781 (2016)). Often the underlying mechanism of action of psychobiotic-derived neurotransmitters is indirect. For example, local stimulation of the vagus nerve in the gastrointestinal tract allows for action at a distance in the brain. Certain gastrointestinal tract bacteria have been reported to produce a range of neurotransmitters, including dopamine, through the metabolism of indigestible fiber. (Sarkar et al., 2016). Therefore, it is thought that the pet food compositions disclosed herein may lead to an increased level of dopamine by increasing the proportions of Lactobacilli and Bifidobacteria in the gastrointestinal tracts of animals who consume the pet food composition, whereupon vagal stimulation offers opportunity to improved mental state by increasing the blood levels of dopamine sulfate. Accordingly, in certain embodiments, the pet food compositions disclosed herein increase the amount of dopamine sulfate in an animal that consumes the pet food composition. In certain embodiments, the amount of dopamine sulfate may be measured in the blood of the animal, such as in the serum.

In certain embodiments of the pet food compositions and methods disclosed herein, the animal consuming the pet food composition consumes at least about 2.5 g of resistant starch per kg of animal per day, such as between about 2.5 g to about 4.7 g of resistant starch per kg of animal per day.

In addition to the resistant starch, the pet food compositions disclosed herein may further comprise additional ingredients, such as fats, carbohydrates, proteins, fibers, and nutritional balancing agents. In certain embodiments, an additional fat and carbohydrate ingredient may be obtained from a variety of sources, such as at least one of animal fat, fish oil, vegetable oil, meat, meat by-products, grains, other animal or plant sources.

In certain embodiments, the pet food compositions disclosed herein may further comprise at least one protein source. Suitable protein sources may be selected from any suitable animal or vegetable source. For example, suitable protein sources may include at least one of poultry meal, poultry by-product meal, chicken meal, chicken by-product meal, lamb meal, meat and meat bone, fish meal, soy bean meal, soy protein concentrates, milk proteins, corn gluten meal, wheat gluten, and gluten. The starch source may also be a source of protein.

In certain embodiments, the pet food compositions disclosed herein may further comprise at least one fiber source. Fiber sources may, for example, be chosen from at least one vegetable fiber source, such as cellulose, beet pulp, peanut hulls, and soy fiber.

In certain embodiments the pet food compositions disclosed herein further comprise nutritional balancing agents. Nutritional balancing agents may be obtained from a variety of sources known to skilled artisans, for example, vitamin and mineral supplements and food ingredients. Vitamins and minerals can be included in amounts required to avoid deficiencies and maintain health. These amounts are readily available in the art. The American Feed Control Officials (AAFCO) provides recommended amounts of such nutrients for dogs and cats. Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

In certain embodiments, the pet food compositions disclosed herein may comprise additional ingredients such as fillers, palatability enhancers, binding agents, flavors, stabilizers, emulsifiers, sweeteners, colorants, buffers, salts, coatings, and the like. Stabilizers include substances that tend to increase the shelf life of the compositions such as preservatives, synergists and sequestrants, packaging gases, emulsifiers, thickeners, gelling agents, and humectants. Examples of emulsifiers and/or thickening agents include gelatin, cellulose ethers, starch, starch esters, starch ethers, and modified starches. Specific amounts for each composition component will depend on a variety of factors such as the particular components included in the composition; the species of the animal, the animal's age, body weight, general health, gender, and diet; the animal's consumption rate; the type of disease or condition being treated; and the like.

The pet food compositions disclosed herein may be made by an optimized extrusion method for producing pet food compositions comprising an enhanced amount of resistant starch. The extrusion methods disclosed herein result in a pet food composition that, due to its enhanced levels of resistant starch, increases the levels of colonic lactate by improving redox balance, while concurrently decreasing AGEs and uremic toxins associated with detrimental health outcomes and increasing the levels of dopamine, resulting in potentially beneficial psychobiotic effects.

The extrusion method disclosed herein minimizes the destruction of resistant starch and plant botanicals to allow for delivery of energy substrates to the lower intestinal tract of animals, such as dogs, for metabolism by commensal gastrointestinal microbiota to beneficial lactates. The novel extrusion methods disclosed herein also produce a food composition that allows, inter alia, for an increased preservation of carnosine and decreases the processing-related AGE formation. Although not wishing to be bound by theory, it is thought that high blood glucose levels from the digestion of non-resistant starch in the small intestine may promote endogenous formation of AGE products. Accordingly, the extrusion methods disclosed herein, which result in a pet food composition having enhanced levels of resistant starch, also lowers the levels of AGE products produced by an animal consuming the pet food composition.

Extrusion of food compositions, such as pet food compositions like kibbles, is well known in the art. Food extrusion devices may comprise a preconditioner interconnected to a single, elongated, tubular extruder barrel having an output comprising a die at an end opposite the preconditioner. The die coupled with the output end of the extruder barrel functions to form the shape of the end-product food, such as the kibble, as it emerges from the extruder barrel. Inside the extruder barrel is a single or twin screw, which functions to apply shear forces and convey the food composition forward and through the extruder barrel towards the output and through the die. Steam may be injected into the preconditioner and/or the extruder barrel during processing.

In certain embodiments disclosed herein, pet food raw materials are fed into a preconditioner, wherein liquid, which may include, for example, water, oil, and steam, are added. In certain embodiments, the preconditioned raw materials may be partially cooked. In the preconditioner, the raw materials are mixed and preconditioned to form a dough. Raw materials may comprise any of the ingredients disclosed above, in addition to and include the source of the resistant starch, such as, for example, fats, carbohydrates, proteins, fibers, and nutritional balancing agents. After preconditioning, the dough is directed into the extruder barrel. In certain embodiments, no additional steam is added when the dough is directed into the extruder barrel.

In the extruder barrel, the dough is subjected to the rotating single or twin screw. Inside the extruder barrel, the dough may be subjected to varying levels of temperature, pressure, and shear, all of which may affect the resultant food product. In certain embodiments, the screw may operate at an RPM of less than about 500 RPMs, such less than about 400 RPMs, less than about 300 RPMs, about 270 RPMs, or a range of from about 250 RPMs to about 300 RPMs. In certain embodiments, the extruder barrel may be operated to have a flow rate greater than about 1,000 kg/h, such as greater than about 1,500 kg/h, about 1,800 kg/h, or ranging from about 1,500 kg/h to about 2,000 kg/h.

As the dough emerges out of the extruder barrel from the die, it may be formed into the final pet food composition product, such as a kibble or other desired shape. The final pet food composition may also expand to a certain degree, which may depend upon many factors, including the amount of energy imparted to the food composition in the extruder barrel, the amount of moisture in the food composition, and the shape of the die.

During the extrusion process, specific mechanical energy is applied, for example in the form of shear mixing. As used herein, the term "Specific Mechanical Energy" (SME) refers to a measure of the mechanical energy put into the extradate in an extruder device, for example from the motor of the extruder. SME is a measure of the energy going into the extrusion system per unit mass and may be measured, for example, in terms of W·h/kg. In a typical food extrusion process involving high shear mixing, SME may range from about 40 W·h/kg to about 50 W·h/kg, such as from about 48 W·h/kg, or, for example, more than about 40 W·h/kg or more than about 45 W·h/kg.

In the extrusion methods disclosed herein, however, low shear mixing may be used. For low shear mixing according to the methods disclosed herein, the SME may be less than about 40 W·h/kg, such as less than about 30 W·h/kg, less than about 25 W·h/kg, less than about 20 W·h/kg, less than about 15 W·h/kg, or about 10 W·h/kg. In certain embodiments, for low shear mixing, the SME may range from about 10 W·h/kg to about 40 W·h/kg, such as from about 10 W·h/kg to about 15 W·h/kg. Under the low shear mixing conditions disclosed herein, the pet food composition retains enhanced levels of resistant starch, such as, for example, at least about 7% resistant starch based on the total amount of the pet food composition.

As used herein, the term "Specific Thermal Energy" (STE) refers to the energy in the form of heat, such as from steam, put into the extrudate in an extruder device. Like SME, STE is a measure of the energy going into the extrusion system per unit mass and may be measured, for example, in terms of W·h/kg. In a typical extrusion process involving high shear mixing, STE may range from about 40 W·h/kg to about 50 W·h/kg, such as from about 40 W·h/kg to about 45 W·h/kg or, in certain embodiments of a typical extrusion process, the STE may be at least about 40 W·h/kg. In certain food extrusion processes involving high shear mixing, the ratio of the SME to STE may be approximately 1, and in certain food extrusion processes involving high shear mixing, the ratio of the SME to STE may be greater than 1.

In the extrusion methods disclosed herein, however, which comprise low shear mixing, according to certain embodiments, the STE may range from about 40 W·h/kg to about 50 W·h/kg, such as from about 40 W·h/kg to about 45 W·h/kg or about 42 W·h/kg or, in certain embodiments, less than about 45 W·h/kg. In certain embodiments of the extrusion methods disclosed herein involving low shear mixing, the ratio of the SME to STE is less than 1, such as less than about 0.5, less than about 0.33, or less than about 0.25.

In certain embodiments of the methods disclosed herein, the sum of the specific mechanical energy and the specific thermal energy of the extrusion device may be less than about 100 W·h/kg, such as less than about 75 W·h/kg, less than about 60 W·h/kg, less than about 50 W·h/kg, or less than about 60 W·h/kg.

In certain embodiments of the methods disclosed herein comprising low shear mixing, the barrel temperature of the extruder barrel may range from about 70° C. to about 125° C. The extruder device may, in certain embodiments, further comprise a back pressure valve operably connected to the extruder barrel that can range from 0% open (fully closed) to 100% open (fully open). In certain embodiments disclosed herein, the back pressure valve is closed.

Disclosed herein are methods of making a pet food composition using low shear extrusion parameters, comprising providing pet food raw materials for extrusion and extruding the raw materials using an extrusion device. In certain embodiments, the raw materials are first preconditioned into a dough. In certain embodiments of the methods disclosed herein, the specific mechanical energy of the extrusion device is less than about 25 W·h/kg and the pet food composition produced by the extrusion method results in a pet food composition comprising resistant starch in an amount of at least about 7% by weight based on the total weight of the pet food composition.

Further disclosed herein are extruded pet food compositions comprising resistant starch in an amount of at least about 7%, such as about 7% to about 30%, at least about 10%, about 9% to about 13%, or about 7% to about 20%, by weight based on the total weight of the pet food composition. As used herein, the term "extruded pet food composition" refers to a pet food composition formulated from raw pet food materials that have been processed in an extrusion device using specific mechanical and thermal energy.

In certain embodiments of the methods disclosed herein, an animal consuming a pet food composition as disclosed herein may consume the pet food composition in an amount of at least about 2.5 g of resistant starch, such as at least about 3 g, at least about 3.5 g, at least about 4 g, at least about 4.5 g, or at least about 5 g of resistant starch per kg of animal per day.

Moreover, disclosed herein are methods for increasing dopamine sulfate, for example in the blood, in animals, comprising feeding the animal a pet food composition as disclosed herein in an amount of at least about 2.5 g of resistant starch, such as at least about 3 g, at least about 3.5 g, at least about 4 g, or at least about 4.5 g, of resistant starch per kg of animal per day. Further disclosed herein are methods for increase carnosine levels in animals, comprising feeding the animal a pet food composition as disclosed herein in an amount of at least about 2.5 g of resistant starch, such as at least about 3 g, at least about 3.5 g, at least about 4 g, at least about 4.5 g, at least about 5 g, at least about 5.5 g, at least about 6 g, or at least about 7 g of resistant starch per kg of animal per day.

The pet food compositions disclosed herein can be fabricated into any form desired, including, for example, kibbles, biscuits, and snack products.

Unless otherwise specified, all percentages and amounts expressed herein and elsewhere in the specification should be understood to refer to percentages by weight. The amounts given are based on the active weight of the material.

EXAMPLES

Example 1, Part A—Preparation of Control and Test Diets

A Test Diet and a Control Diet were formulated according to the American Association of Feed Control Officials (AAFCO) nutrition recommendations. The formulations were produced by extrusion, dried, and coated with palatants. Both the Test Diet and the Control Diet were a simple canine maintenance formulation and were the same formulation, as shown below in Table 1.

TABLE 1

Test Diet and Control Diet Formulation Comparison

| Description | Test Diet (% wt) | Control Diet (% wt) |
| --- | --- | --- |
| Corn, yellow whole | 41.72 | 41.72 |
| Rice, brewers | 13.76 | 13.76 |
| Eggs, dried pelleted | 13.76 | 13.76 |
| Poultry by-product meal, reg ash | 10.27 | 10.27 |
| Corn, gluten meal | 7.87 | 7.87 |
| Pork fat, Choice white grease | 3.04 | 3.04 |
| Cellulose, pelleted | 1.90 | 1.90 |
| Lactic acid, blend 84% | 1.50 | 1.50 |
| Other | QS | QS |

For the Control Diet, the kibbles were prepared under high shear extrusion parameters. The raw ingredients were fed into a preconditioner wherein steam was added at 73.2 kg/h and 11% steam pressure (SP), achieving a temperature of 98.8° C. at the end of the preconditioner. Water content was 27.5% with a preconditioner processing rate of 858.4 kg/h. The preconditioned dough was then fed into the extrusion barrel, wherein the screw operated at 500 RPM at a 55% load. The temperature in the extrusion barrel varied from 69.4° C. to 142.8° C. No steam was added to the extrusion barrel, resulting in flow rate of 858.4 kg/h in the barrel at moisture content of 27.5% $H_2O$. The back pressure valve was closed (0% open), and the temperature at the die output was 131.6° C., resulting in −44.2 kg/h steam evaporation and a kibble product of 23.5% $H_2O$. The Specific Mechanical Energy (SME) for the high shear parameters was calculated to be 48 W·h/kg, and the Specific Thermal Energy (STE) was calculated to be 41 W·h/kg, for a Total Energy of 89 W·h/kg.

For the Test Diet, the kibbles were prepared under low shear extrusion parameters. The raw ingredients were fed into a preconditioner wherein steam was added at 138.8 kg/h and 10% SP, achieving a temperature of 101.3° C. Water content was 25.0% at a rate of 1,827.5 kg/h. The preconditioned dough was then fed into the extrusion barrel, wherein the screw operated at 270 RPM at a 24% load. The temperature in the extrusion barrel varied from 71.7° C. to 123.7° C. No steam was added to the extrusion barrel, resulting in flow rate of 1,827.5 kg/h in the barrel and a moisture content of 25.0% $H_2O$. The back pressure valve was 100% open, and the temperature at the die output was 110.5° C., resulting in −50.0 kg/h steam evaporation and a kibble product of 22.9% $H_2O$. The SME for the low shear parameters was calculated to be 10 W·h/kg, and the STE was calculated to be 42 W·h/kg, for a Total Energy of 51 W·h/kg. Accordingly, there was approximately a 4-fold reduction in Mechanical Shear Energy (MSE) under the low shear parameters for the Test Diet as compared to the high shear parameters for the Control Diet.

Figure 1:
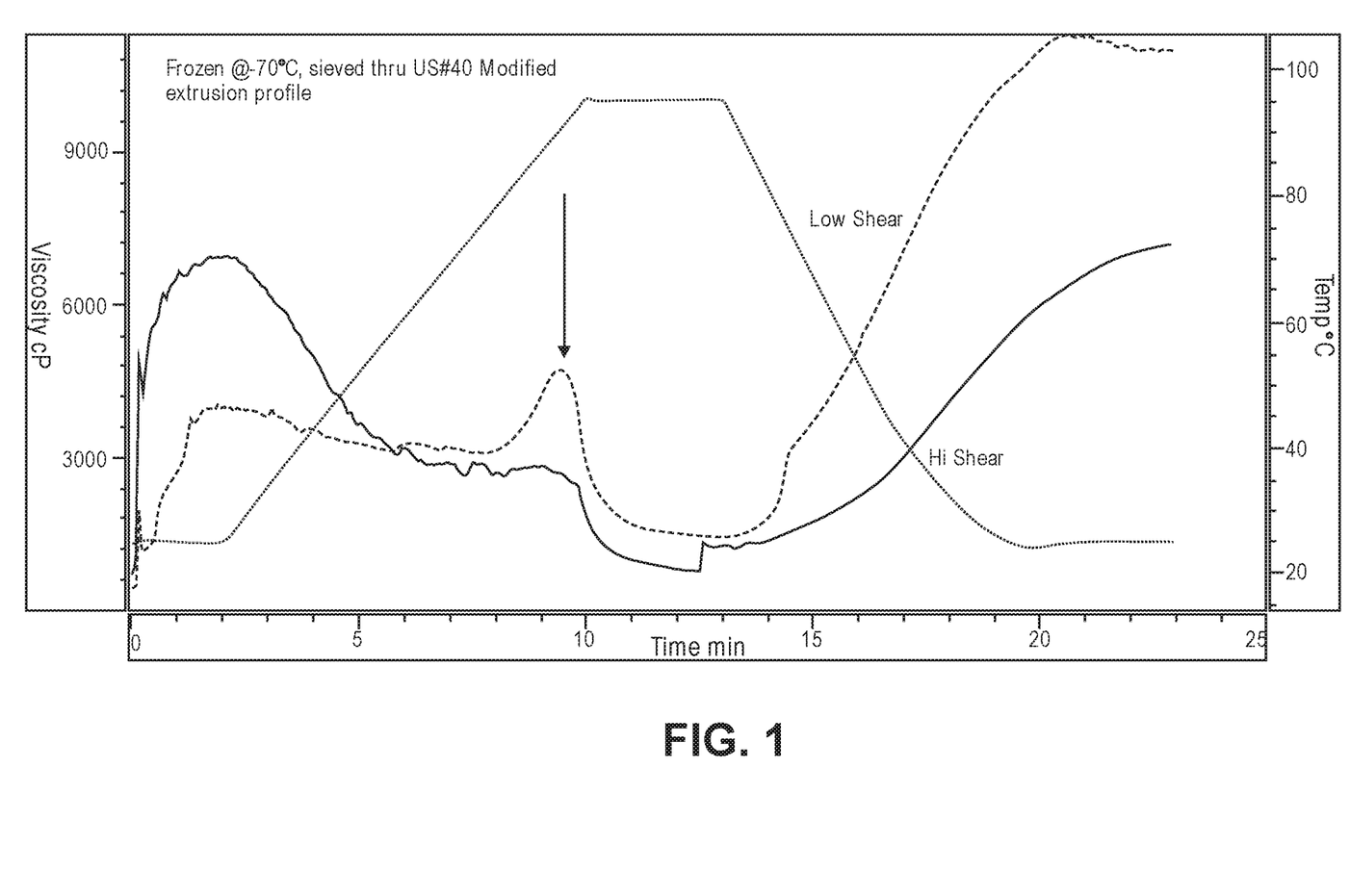
FIG. 1 is a graph showing the Relative Viscosity Analysis for a sample of Test Diet prepared under low shear extrusion conditions having an enhanced amount of resistant starch and versus a Control Diet prepared under high shear extrusion conditions. The resistant starch peak of the Test Diet is noted with an arrow.

The reduction in MSE resulted in significant preservation of the macromolecular structure of the raw ingredients, as indicated by an enhanced level of resistant starch in the Test Diet relative to the Control Diet produced under high MSE conditions. In a Relative Viscosity Analysis, a graph of which is shown in FIG. 1, the Test Diet exhibited a peak where the Control Diet did not, showing the enhanced presence of resistant starch in the Test Diet. The lower viscosity at low temperatures at the beginning of the curve indicates a high undegraded starch content of the Test Diet. As the temperature rises, the higher viscosity peak on the Test Diet indicates a greater content of resistant starch being released. Finally, the higher viscosity peak of the Test Diet at the later cooler temperatures indicates higher resistant starch content, which enabled it to remain more viscous.

Based on the high shear extrusion parameters used to produce the Control Diet, it is estimated that the Control Diet comprised about 2% by weight of resistant starch. Based on the low shear extrusion parameters used to produce the Test Diet, it is estimated that the Test Diet comprised about 28% by weight of resistant starch.

Example 1, Part B—Feeding of Control and Test Diets

Institutional Animal Care and Use Committee (IACUC)-approved Digestibility Assessment protocols were performed using healthy canines on existing panels. A digestibility panel, inclusive of stool assessment, was performed.

In addition to digestibility panels, an IACUC-approved clinical dietary intervention protocol was implemented which enrolled healthy canine subjects randomized to two groups based on age, weight, and gender. Canines were assessed by blood and fecal markers of biochemical and clinical health. The study was a caretaker-blinded, longitudinal design.

Stools were collected after six weeks of consuming the Control and Test Diets. Stools were assessed by Hill's Visual Stool Scale, which ranks the subjective desirability of stools from essentially liquid (Score 1) to exemplarily firm (Score 5). After scoring, within 30 minutes of defecation the stools were homogenized extensively and then portions were aliquoted into cryo containers before being flash frozen into liquid nitrogen for metabolic endpoints (e.g., lactates, pyruvates, AGE, carnosine).

As discussed above, the Test Diet differed from the Control Diet by the 4-fold reduction in Mechanical Shear Energy, which resulted in a dramatic preservation of resistant starch. See the Relative Viscosity Analysis at FIG. 1. The food was analyzed and found to be equivalent in PGP-22 T1 terms of protein, fat, fiber, moisture, ash, and energy density. See Table 2 below.

TABLE 2

Feed Analytical Results of Control and Test Diets

| | Analysis | Mean | | Analysis | Mean |
|---|---|---|---|---|---|
| Control Diet | % Moisture | 7.6 | Test Diet | % Moisture | 7.5 |
| | % Fat | 12.2 | | % Fat | 13.4 |
| | % Protein | 23.4 | | % Protein | 23.4 |
| | % NDF Fiber | 7.4 | | % NDF Fiber | 7.2 |
| | % Ash | 5.8 | | % Ash | 5.8 |
| | % Crude Fiber | 2.7 | | % Grade Fiber | 2.6 |
| | Kcal/lb | 2177 | | Kcal/lb | 2054 |

Digestibility of the Test Diet was essentially equivalent to the Control Diet, except for about a 2% decrease in protein digestibility, as shown in Table 3 below. Additionally, it may be noted that the digestibility of fiber in the test diet was increased over digestibility of fiber in the control diet. This increase may indicate that the process used to prepare the test diet resulted in fiber that had an increased fermentability by gut bacteria.

TABLE 3

Digestibility Comparison of Control and Test Diets

| | Result | Mean | | Result | Mean |
|---|---|---|---|---|---|
| Control Diet | Apparent dry matter digestibility, % | 85.9 | Test Diet | Apparent dry matter digestibility, % | 85.2 |
| | Apparent protein digestibility, % | 88.4 | | Apparent protein digestibility, % | 86.6 |
| | True protein digestibility, % | 95.4 | | True protein digestibility, % | 91.6 |
| | Apparent fat digestibility, % | 92.2 | | Apparent fat digestibility, % | 93.3 |
| | Apparent fiber digestibility, % | 20.1 | | Apparent fiber digestibility, % | 28 |
| | Apparent carbohydrate digestibility, % | 92 | | Apparent carbohydrate digestibility, % | 90 |
| | Diet gross energy, kcal/kg | 4795 | | Diet gross energy, kcal/kg | 4523 |
| | Diet digestible energy, kcal/kg | 4254 | | Diet digestible energy, kcal/kg | 3980 |
| | % NFE, calories | 48.3 | | % NFE calories | 46.2 |
| | % Protein calories | 23.9 | | % Protein calories | 23.2 |
| | % Fat calories | 27.8 | | % Fat calories | 30.6 |
| | Initial body weight, kg | 9.62 | | Initial body weight, kg | 13.23 |
| | Final body weight, kg | 9.37 | | Final body weight, kg | 13.27 |
| | Average daily intake, g | 138.5 | | Average daily intake, g | 241.03 |
| | Average stool rating | 4.8 | | Average stool rating | 4 |
| | Apparent energy digestibility, % | 88.71 | | Apparent energy digestibility, % | 87.98 |
| | Diet metab. energy, kcal/kg AAFCO tested | 3995 | | Diet metab. energy, kcal/kg AAFCO tested | 3726 |
| | Apparent vital nutrient digestibility', % | 92.7 | | Apparent vital nutrient digestibility, % | 91.2 |

As shown in Table 3, the main differences between the Control Diet and the Test Diet resided in the metabolizable energy, which was lower for the Test Diet than the Control Diet, and food intake quantity, which was higher for the test diet than for the control diet.

Figure 2:
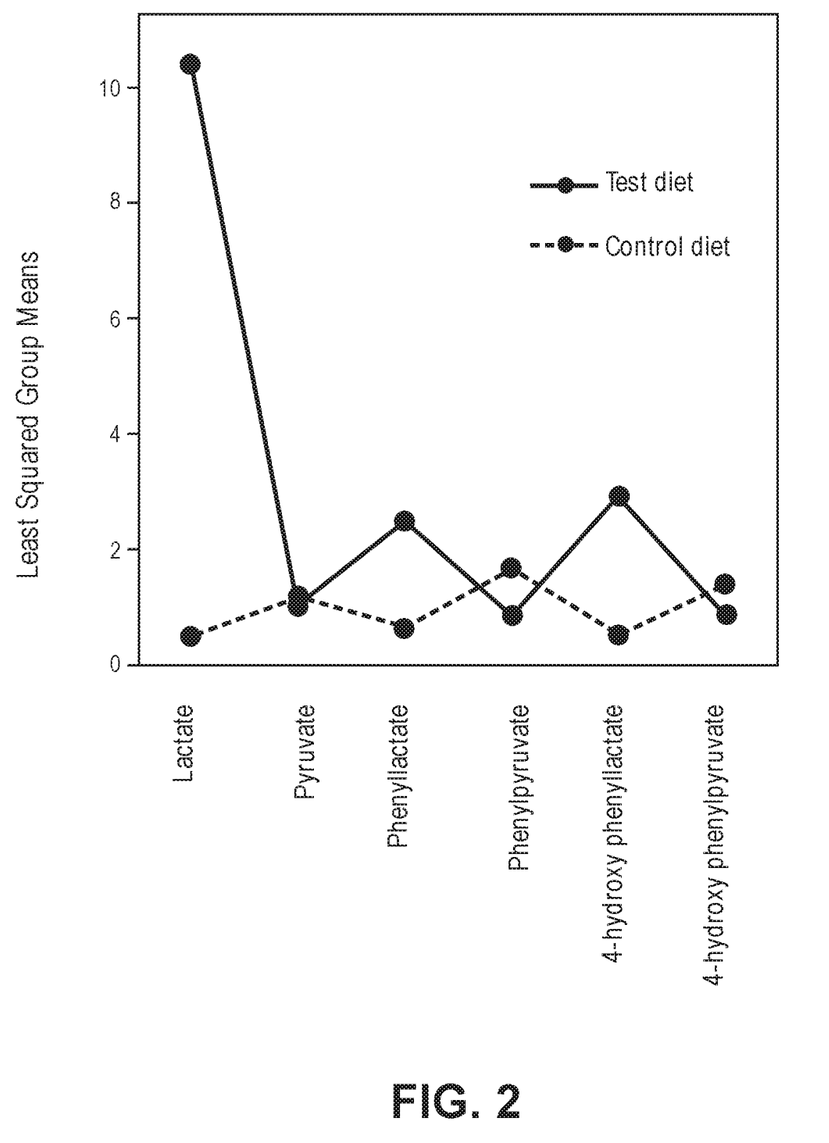
FIG. 2 is a graph indicating the fecal levels of the following analytes in terms of least square group means in canines who consumed a Test Diet prepared under low shear extrusion conditions versus canines who consumed a Control Diet prepared under high shear extrusion conditions: lactate, pyruvate, phenyllactate, phenylpryuvate, 4-hydroxyphenyllactate, and 4-hydroxyphenylpyruvate.

Fecal lactate values were measured both for canines who consumed the Test Diet for six weeks and canines who consumed the Control Diet for six weeks. The fecal lactate levels are summarized in Table 4 below, expressed in Normalized Relative Levels, wherein the sample with the median value is set to 1 and remaining samples are a ratio to the mean value sample.

herein. This effect of the low shear method disclosed herein is not limited to lactate, but instead appears to be a global effect on NADH:hydroxyl-keto redox couples. FIG. 2 indicates that in every measured instance, the keto congener was reduced while the hydroxyl congener was increased on the Test Diet. Lactates (keto) were reduced, while pyruvates (hydroxyls) were oxidized. See Tables 5 and 6 below, expressed in Normalized Relative Levels.

TABLE 5

| Fecal Metabolite Levels for Canines Consuming Test and Control Diets | | | | | |
|---|---|---|---|---|---|
| Fecal pyruvate for Canines consuming Test Diet | Fecal pyruvate for Canines consuming Control Diet | Fecal phenylpyruvate for Canines consuming Test Diet | Fecal phenylpyruvate for Canines consuming Control Diet | Fecal 4-hydroxy phenylpyruvate for Canines consuming Test Diet | Fecal 4-hydroxy phenylpyruvate for Canines consuming Control Diet |
| 1.076 | 1.092 | 0.93 | 1.91 | 0.83 | 1.35 |
| 1.24 | 0.57 | 0.95 | 0.86 | 0.94 | 0.98 |
| 0.90 | 1.33 | 0.28 | 2.23 | 0.62 | 1.33 |
| 1.35 | 2.15 | 0.53 | 7.34 | 0.60 | 5.57 |
| 0.80 | 1.40 | 0.56 | 2.07 | 0.51 | 2.13 |
| 0.86 | 1.22 | 1.38 | 1.59 | 1.11 | 1.89 |
| 1.32 | 0.73 | 0.90 | 1.39 | 1.32 | 0.77 |
| 1.06 | 0.91 | 0.70 | 0.80 | 0.91 | 1.00 |
| 1.03 | 1.68 | 0.59 | 1.22 | 0.92 | 1.12 |
| 1.07 | 1.49 | 0.80 | 1.71 | 0.73 | 1.95 |
| 1.10 | 1.18 | 0.37 | 0.25 | 0.37 | 0.42 |
| 1.02 | 0.98 | 0.91 | 1.15 | 1.10 | 0.74 |
| 1.17 | 0.93 | 0.78 | 0.55 | 0.58 | 0.60 |
| 1.16 | 1.32 | 2.35 | 1.64 | 1.57 | 0.67 |
| 1.06 | 0.53 | 0.72 | 0.64 | 0.74 | 0.56 |
| 0.61 | 1.35 | 0.44 | 1.46 | 0.85 | 1.25 |

TABLE 4

| Fecal Lactate Levels for Canines Consuming Test and Control Diets | |
|---|---|
| Fecal lactate for Canines consuming Test Diet | Fecal lactate for Canines consuming Control Diet |
| 4.36 | 0.38 |
| 20.39 | 0.71 |
| 0.23 | 0.51 |
| 23.47 | 0.62 |
| 1.11 | 0.32 |
| 7.89 | 0.30 |
| 40.16 | 0.29 |
| 15.44 | 0.31 |
| 0.97 | 0.48 |
| 5.49 | 0.51 |
| 20.78 | 0.45 |
| 17.26 | 0.25 |
| 4.82 | 0.49 |
| 0.37 | 0.65 |
| 2.01 | 1.06 |
| 1.67 | 0.59 |

A significant effect of the Test Diet was found on colonic lactate production by commensal microbiota; there was up to a 40-fold increase in lactate measured in feces from dogs consuming the Test Diet relative to the level of lactate from feces of dogs consuming the Control Diet, which was not produced with the low shear extrusion method disclosed

TABLE 6

| Fecal Metabolite Levels for Canines Consuming Test and Control Diets | | | |
|---|---|---|---|
| Fecal phenyllactate for Canines consuming Test Diet | Fecal phenyllactate for Canines consuming Control Diet | Fecal 4-hydroxy phenyllactate for Canines consuming Test Diet | Fecal 4-hydroxy phenyllactate for Canines consuming Control Diet |
| 2.20 | 0.45 | 2.40 | 0.29 |
| 2.38 | 1.19 | 2.51 | 0.84 |
| 0.30 | 0.57 | 0.22 | 0.40 |
| 4.50 | 1.33 | 5.45 | 0.74 |
| 0.72 | 0.45 | 0.74 | 0.21 |
| 1.68 | 0.42 | 2.06 | 0.25 |
| 8.45 | 0.48 | 11.19 | 0.26 |
| 1.68 | 0.17 | 2.65 | 0.16 |
| 1.71 | 0.56 | 2.47 | 0.15 |
| 2.11 | 0.40 | 2.58 | 0.41 |
| 5.42 | 1.34 | 4.09 | 2.40 |
| 4.23 | 0.32 | 3.80 | 0.16 |
| 1.91 | 0.28 | 3.24 | 0.19 |
| 0.54 | 0.62 | 0.39 | 0.36 |
| 1.19 | 0.75 | 0.84 | 0.35 |
| 0.84 | 0.87 | 1.64 | 0.74 |

As shown below in Table 7, the normalized relative levels of carnosine, an AGE scavenger, in feces and serum of canines fed the pet food composition disclosed herein were also significantly higher than in canines fed a control food.

TABLE 7

Fecal and Serum Carnosine Levels in Canines Consuming Test and Control Diets

| Fecal Carnosine for Canines consuming Test Diet | Fecal Carnosine for Canines consuming Control Diet | Serum Carnosine for Canines consuming Test Diet | Serum Carnosine for Canines consuming Control Diet |
|---|---|---|---|
| 1.39 | 0.95 | 1.18 | 1.02 |
| 2.93 | 1.10 | 1.31 | 0.88 |
| 0.51 | 0.75 | 0.99 | 0.91 |
| 1.35 | 0.19 | 1.43 | 0.78 |
| 0.74 | 0.28 | 0.83 | 1.06 |
| 2.40 | 0.62 | 0.99 | 0.79 |
| 2.95 | 0.21 | 1.06 | 0.68 |
| 1.54 | 0.19 | 1.43 | 0.85 |
| 1.60 | 0.85 | 1.35 | 0.91 |
| 1.17 | 0.58 | 1.30 | 0.85 |
| 1.65 | 0.95 | 1.58 | 1.21 |
| 2.60 | 0.19 | 1.33 | 1.53 |
| 0.59 | 0.50 | 0.94 | 1.23 |
| 0.66 | 0.62 | 0.87 | 0.76 |
| 0.60 | 2.16 | 0.98 | 1.29 |
| 1.68 | 1.43 | 1.08 | 1.02 |

The increase levels of carnosine would lead one to theorize that AGE compounds would commensurately be reduced in canines consuming the Test Diet. Indeed, the Test Diet also reduced gastrointestinal tract exposure to AGE compounds in canines, relative to the Control Diet, for three common AGE compounds, including carboxymethyllysine, carboxyethyllysine, and pyrraline, as shown below in Table 8 and expressed Normalized Relative Levels.

TABLE 8

Fecal AGE Levels in Canines Consuming Test and Control Diets

| Fecal N6-carboxy-methyllysine for Canines consuming Test Diet | Fecal N6-carboxy-methyllysine for Canines consuming Control Diet | Fecal N6-carboxy-ethyllysine for Canines consuming Test Diet | Fecal N6-carboxy-ethyllysine for Canines consuming Control Diet | Fecal pyrraline for Canines consuming Test Diet | Fecal pyrraline for Canines consuming Control Diet |
|---|---|---|---|---|---|
| 0.81 | 1.55 | 0.65 | 1.16 | 0.77 | 0.93 |
| 1.07 | 1.15 | 1.02 | 0.60 | 0.67 | 0.37 |
| 0.61 | 1.87 | 0.98 | 1.35 | 0.38 | 0.98 |
| 0.77 | 1.85 | 0.96 | 1.15 | 0.70 | 0.53 |
| 0.59 | 1.405 | 0.93 | 1.73 | 0.42 | 0.79 |
| 1.15 | 1.04 | 0.97 | 0.90 | 0.57 | 0.48 |
| 1.99 | 0.98 | 1.32 | 1.15 | 0.74 | 0.52 |
| 0.92 | 0.75 | 1.03 | 1.09 | 0.73 | 0.48 |
| 1.10 | 1.24 | 0.89 | 1.62 | 0.57 | 0.88 |
| 1.11 | 1.80 | 1.10 | 1.87 | 0.52 | 0.72 |
| 0.412 | 1.42 | 1.22 | 1.43 | 0.65 | 0.91 |
| 1.22 | 2.04 | 1.03 | 2.01 | 0.82 | 0.83 |
| 1.01 | 1.00 | 1.50 | 1.10 | 0.72 | 0.66 |
| 1.23 | 1.24 | 0.98 | 1.29 | 0.56 | 0.89 |
| 0.74 | 2.34 | 0.93 | 1.65 | 0.60 | 0.85 |
| 1.00 | 1.37 | 0.98 | 1.21 | 0.43 | 1.15 |

Figure 3:
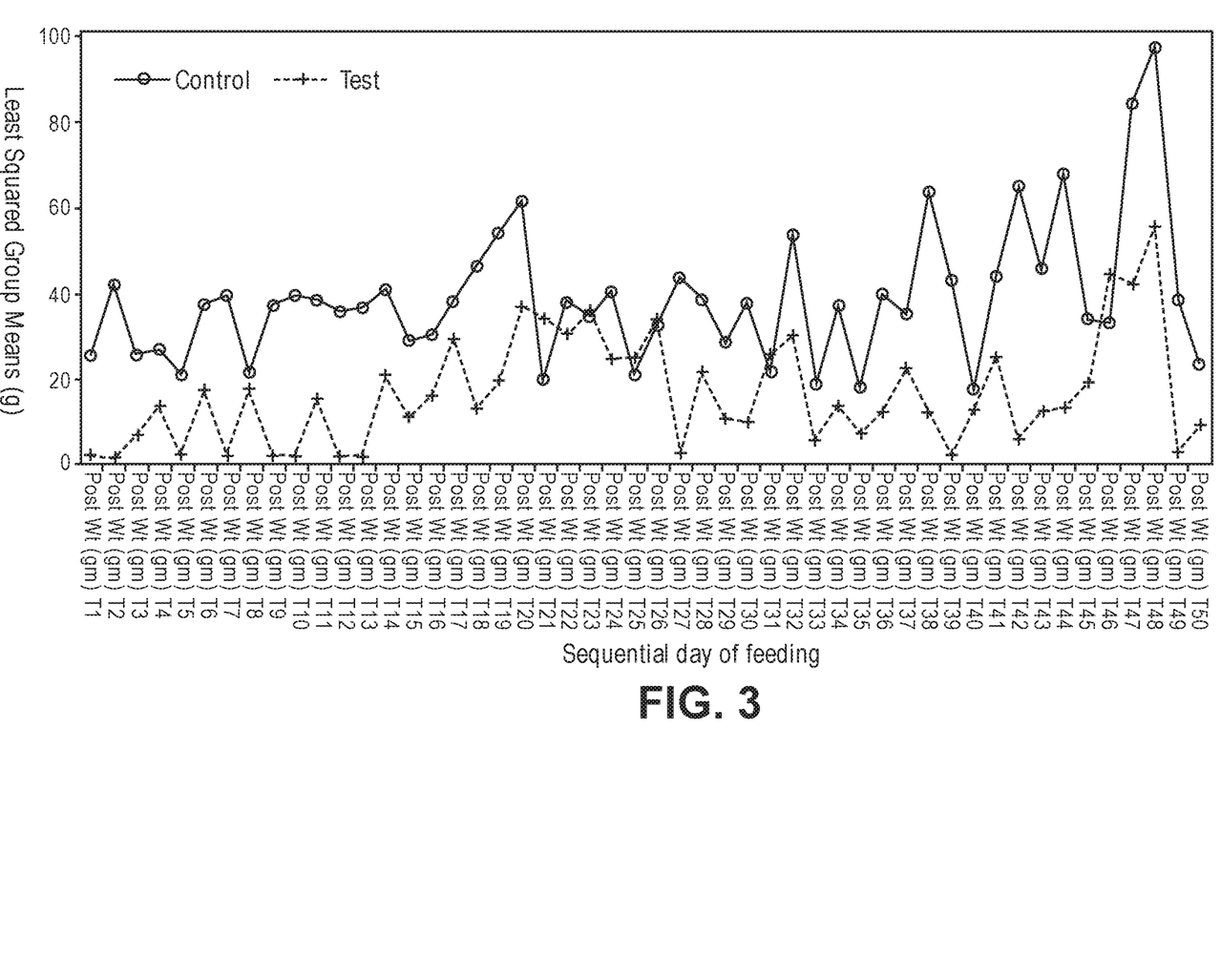
FIG. 3 is a graph showing the mass in grams of returned kibble from canine subjects offered the Test Diet and canine subjects offered the Control Diet.

While AGE exposure is detrimental to health, they are also flavor molecules. Accordingly, one might assume that a diet reduced in AGE would be less palatable. Thus, it could be hypothesized that the Test Diet should suffer from increased kibble rejection and reduced energy intake for canine subjects. In fact, the data indicated that there was no detrimental impact of reduced AGE on food acceptance. As shown in FIG. 3, the amount of kibble rejected by canines eating the Test Diet was lower than the amount rejected by canines consuming the Control Diet. Moreover, the body weights of the subjects were not significantly different from the beginning to the end of the study (p>0.05, not shown).

Accordingly, it is concluded that using a single formula, extrusion-based optimization of preservation of resistant starch and dipeptide carnosine can improve redox balance of the colonic environment of canines. Further, levels of AGE were decreased after consuming the Test Diet, indicating the potential to improve health. Finally, despite reduced AGEs, which can act as flavor molecules, the Test Diet disclosed herein retained its palatability and kibble acceptance.

Example 2

A study was completed using 36 senior dogs between the ages of 8 and 13 years. The Test Diet contained brewer's rice and corn as the sole sources of grain at a ratio of approximately 1:5. The Control Diet contained a variety of whole grains such as sorghum, wheat, barley, and oat, as well as 20% of the corn in the Test Food. The two diets had a similar nutrient profile except for the grains, as shown below in Table 9.

TABLE 9

Comparison of the Test Diet and the Control Diet

| Nutrient | Test Diet | Control Diet |
|---|---|---|
| Moisture | 7.6% | 8.91% |
| Ash | 4.52% | 4.8% |
| Crude fat | 12.67% | 12.98% |
| Crude fiber | 1.5% | 1.9% |

TABLE 9-continued

Comparison of the Test Diet and the Control Diet

| Nutrient | Test Diet | Control Diet |
|---|---|---|
| Crude protein | 19.6% | 17.77% |
| Carbohydrates | 54.11% | 53.64% |

*Carbohydrates (nitrogen-free extract) = 100% − (% protein + % fat + % fiber + % ash + % moisture)

All dogs were provided with the Test Diet for 30 days and were then divided into two groups. One of the two groups received the Control Diet for the next 30 days, while, during the same period, the other group was fed another food having a distinct formulation. At the end of this period, both groups were put on the Test Diet for 30 days, and a cross-over was performed to feed Control Diet or the food with distinct formulation for another 30 days. Finally, both groups received the Test Diet for 30 days. Blood and fecal samples were collected at the end of each 30-day period for analyzing certain metabolites and gut microbial populations. Reported herein are the differences in the outcomes after feeding the Test Diet with those after feeding the Control Diet.

As shown in Table 10, the Test Diet induced a significant increase in the fecal proportions of the beneficial bacterial genera *Lactobacillus* ($P<0.0001$) and *Bifidobacterium* ($P=0.0168$) in senior dogs. Furthermore, the Test Diet induced a significant decrease in the relative abundance of *Megamonas* ($P=0.0004$), largely consisting of disease causing bacteria.

TABLE 10

Comparison of Fecal Bacteria after Consuming Test Diet and Control Diet

| Sample Dog # | Fecal Lactobacillus after Test Diet (g) | Fecal Lactobacillus after Control Diet (g) | Fecal Bifidobacterium after Test Diet (g) | Fecal Bifidobacterium after Control Diet (g) | Fecal Megamonas after Test Diet (g) | Fecal Megamonas after Control Diet (g) |
|---|---|---|---|---|---|---|
| 1 | 34.82 | 28.36 | 7.65 | 31.52 | 2.77 | 2.56 |
| 2 | 8.73 | 7.74 | 28.49 | 13.00 | 0.11 | 2.45 |
| 3 | 27.36 | 12.23 | 15.72 | 15.31 | 1.00 | 0.50 |
| 4 | 0.04 | 16.11 | 0.04 | 7.23 | 4.64 | 4.16 |
| 5 | 21.93 | 0.21 | 21.59 | 7.85 | 0.76 | 2.52 |
| 6 | 27.75 | 0.85 | 0.87 | 0.59 | 15.46 | 33.36 |
| 7 | 38.07 | 11.92 | 9.50 | 13.06 | 1.02 | 3.74 |
| 8 | 7.73 | 0.08 | 9.78 | 1.22 | 2.03 | 15.42 |
| 9 | 39.20 | 6.55 | 8.19 | 5.76 | 2.87 | 12.19 |
| 10 | 5.93 | 0.34 | 23.41 | 2.34 | 0.51 | 4.60 |
| 11 | 16.21 | 13.61 | 12.90 | 16.73 | 0.33 | 2.09 |
| 12 | 0.03 | 0.01 | 0.01 | 0.10 | 5.51 | 32.79 |
| 13 | 38.02 | 7.36 | 19.91 | 4.72 | 0.01 | 0.78 |
| 14 | 3.00 | 10.23 | 19.98 | 14.59 | 1.94 | 4.70 |
| 15 | 35.71 | 3.91 | 31.16 | 19.37 | 0.74 | 22.68 |
| 16 | 59.77 | 9.61 | 4.68 | 9.09 | 0.71 | 7.82 |
| 17 | 3.54 | 3.13 | 3.80 | 0.81 | 25.11 | 23.46 |
| 18 | 7.07 | 9.02 | 3.48 | 10.50 | 1.01 | 12.96 |
| 19 | 0.08 | 0.06 | 0.09 | 0.08 | 13.95 | 15.94 |
| 20 | 3.08 | 6.87 | 0.42 | 0.48 | 8.38 | 17.95 |
| 21 | 36.23 | 10.79 | 22.99 | 8.38 | 0.80 | 1.95 |
| 22 | 0.02 | 0.03 | 0.01 | 0.04 | 38.23 | 32.74 |
| 23 | 25.26 | 7.58 | 19.00 | 12.41 | 0.39 | 4.06 |
| 24 | 13.15 | 1.44 | 20.40 | 6.55 | 0.26 | 2.86 |
| 25 | 31.23 | 14.47 | 23.69 | 7.04 | 0.54 | 5.03 |
| 26 | 8.87 | 0.87 | 21.07 | 0.09 | 5.72 | 20.68 |
| 27 | 15.12 | 4.06 | 18.35 | 7.25 | 1.97 | 17.51 |
| 28 | 33.03 | 14.64 | 11.48 | 12.39 | 1.61 | 8.36 |
| 29 | 5.92 | 11.08 | 10.37 | 4.11 | 1.96 | 2.02 |
| 30 | 28.99 | 5.75 | 25.31 | 21.39 | 0.23 | 3.74 |
| 31 | 13.52 | 3.23 | 15.60 | 11.16 | 0.20 | 0.36 |
| 32 | 18.54 | 8.13 | 7.05 | 14.56 | 0.41 | 8.52 |
| 33 | 19.21 | 0.01 | 12.05 | 0.02 | 1.93 | 36.06 |
| 34 | 3.57 | 1.50 | 1.25 | 4.46 | 22.74 | 9.74 |
| 35 | 29.01 | 22.68 | 11.78 | 10.54 | 1.16 | 2.33 |
| 36 | 2.73 | 10.95 | 0.68 | 5.83 | 3.02 | 3.07 |

The shift in the gut microbiota was accompanied by significant health benefits in senior dogs by improving levels of metabolites associated with age-related health problems. As shown in Table 11, these metabolites include a decline in the AGEs comprising pyrraline ($P=0.0002$) and N6-carboxymethyllysine ($P=0.0038$); the Test Diet further led to a decline in the uremic toxin 3-methyl catechol sulfate ($P<0.0001$) in the plasma of senior dogs.

TABLE 11

Comparison of Metabolites after Consuming Test Diet and Control Diet

| Sample Dog # | Pyrraline after Test Diet (g) | Pyrraline after Control Diet (g) | N6-carboxymethyllysine after Test Diet (g) | N6-carboxymethyllysine after Control Diet (g) | 3-methyl catechol sulfate after Test Diet (g) | 3-methyl catechol sulfate after Control Diet (g) |
|---|---|---|---|---|---|---|
| 1 | 0.66 | 1.31 | 0.20 | 1.02 | 0.35 | 0.86 |
| 2 | 0.96 | 2.08 | 0.77 | 1.34 | 0.53 | 0.62 |
| 3 | 0.44 | 1.11 | 0.20 | 0.42 | 0.35 | 0.65 |
| 4 | 0.50 | 1.89 | 0.75 | 1.42 | 0.35 | 0.44 |
| 5 | 3.17 | 1.32 | 3.39 | 1.03 | 0.82 | 1.21 |
| 6 | 1.08 | 2.65 | 0.66 | 1.16 | 0.35 | 0.73 |
| 7 | 2.41 | 2.49 | 0.93 | 1.36 | 1.13 | 1.42 |
| 8 | 1.13 | 1.84 | 0.96 | 1.13 | 0.55 | 0.79 |
| 9 | 1.00 | 2.56 | 0.20 | 1.61 | 0.35 | 0.66 |
| 10 | 0.72 | 1.00 | 0.76 | 0.77 | 0.35 | 0.57 |
| 11 | 1.04 | 3.40 | 0.42 | 1.68 | 0.49 | 1.66 |
| 12 | 1.11 | 2.34 | 0.89 | 1.25 | 0.35 | 1.25 |
| 13 | 5.03 | 0.64 | 1.16 | 0.83 | 1.11 | 0.35 |
| 14 | 1.44 | 2.12 | 0.78 | 1.04 | 0.44 | u.52 |
| 15 | 0.97 | 1.72 | 0.77 | 1.03 | 1.06 | 2.30 |
| 16 | 0.93 | 2.22 | 0.64 | 0.80 | 0.74 | 0.81 |
| 17 | 1.64 | 6.21 | 0.83 | 1.22 | 0.35 | 0.86 |
| 18 | 2.34 | 2.80 | 1.63 | 1.36 | 3.44 | 6.29 |
| 19 | 1.33 | 1.78 | 0.33 | 0.84 | 1.28 | 0.41 |
| 20 | 0.55 | 1.73 | 0.73 | 0.81 | 0.35 | 0.35 |

TABLE 11-continued

Comparison of Metabolites after Consuming Test Diet and Control Diet

| Sample Dog # | Pyrraline after Test Diet (g) | Pyralline after Control Diet (g) | N6-carboxy-methyl-lysine after Test Diet (g) | N6-carboxy-methyl-lysine after Control Diet (g) | 3-methyl catechol sulfate after Test Diet (g) | 3-methyl catechol sulfate after Control Diet (g) |
|---|---|---|---|---|---|---|
| 21 | 0.79 | 3.11 | 1.01 | 1.95 | 0.35 | 1.45 |
| 22 | 0.12 | 2.87 | 0.22 | 1.08 | 0.35 | 0.86 |
| 23 | 1.36 | 6.64 | 0.70 | 1.70 | 0.64 | 2.01 |
| 24 | 0.60 | 1.44 | 0.20 | 0.73 | 1.49 | 1.50 |
| 25 | 1.18 | 3.48 | 1.01 | 1.68 | 1.32 | 3.06 |
| 26 | 1.08 | 0.75 | 1.05 | 0.68 | 0.35 | 0.35 |
| 27 | 0.91 | 2.57 | 0.67 | 1.27 | 0.72 | 2.24 |
| 28 | 0.98 | 2.43 | 0.77 | 1.28 | 0.35 | 2.91 |
| 29 | 0.55 | 0.87 | 0.20 | 0.88 | 0.35 | 0.57 |
| 30 | 0.63 | 0.92 | 0.56 | 0.52 | 0.35 | 0.63 |
| 31 | 1.44 | 2.79 | 2.88 | 2.27 | 1.51 | 2.29 |
| 32 | 0.64 | 0.95 | 0.53 | 0.80 | 0.35 | 0.77 |
| 33 | 0.49 | 2.22 | 0.23 | 1.54 | 0.35 | 0.81 |
| 34 | 0.78 | 1.83 | 0.68 | 1.07 | 0.35 | 1.09 |
| 35 | 1.82 | 3.26 | 0.99 | 1.35 | 1.01 | 3.27 |
| 36 | 1.80 | 2.41 | 1.40 | 1.32 | 1.43 | 1.35 |

Finally, the Test Diet led to a significant increase ($P<0.0001$) in the blood levels of dopamine sulfate in senior dogs, as shown in Table 12 below.

TABLE 12

Comparison of Dopamine Sulfate Levels after Consuming Test Diet and Control Diet

| Sample Dog # | Pyrraline after Test Diet (g) | Pyralline after Control Diet (g) |
|---|---|---|
| 1 | 1.16 | 0.61 |
| 2 | 0.76 | 0.61 |
| 3 | 0.70 | 0.62 |
| 4 | 0.83 | 1.05 |
| 5 | 2.49 | 0.45 |
| 6 | 1.18 | 0.62 |
| 7 | 1.85 | 0.62 |
| 8 | 1.54 | 0.70 |
| 9 | 1.04 | 0.91 |
| 10 | 0.96 | 0.46 |
| 11 | 1.14 | 1.14 |
| 12 | 0.99 | 0.44 |
| 13 | 1.26 | 0.35 |
| 14 | 1.53 | 0.52 |
| 15 | 1.86 | 0.70 |
| 16 | 0.92 | 0.49 |
| 17 | 1.36 | 0.63 |
| 18 | 1.31 | 0.47 |
| 19 | 1.76 | 0.76 |
| 20 | 1.19 | 0.46 |
| 21 | 1.92 | 2.04 |
| 22 | 0.90 | 1.02 |
| 23 | 0.85 | 0.75 |
| 24 | 0.87 | 0.40 |
| 25 | 1.56 | 0.88 |
| 26 | 1.09 | 0.49 |
| 27 | 0.88 | 0.52 |
| 28 | 1.96 | 1.28 |
| 29 | 0.90 | 0.30 |
| 30 | 0.90 | 0.28 |
| 31 | 1.84 | 1.18 |
| 32 | 0.79 | 0.38 |
| 33 | 2.05 | 1.23 |
| 34 | 0.93 | 0.45 |
| 35 | 1.44 | 0.72 |
| 36 | 1.52 | 0.95 |

The total carbohydrate (nitrogen-free extract) content of both the Test Diet and Control Diet was approximately 0.54 (Table 9). Therefore, on average, a typical dog consuming 300 grams of food a day consumed about 162 grams of total carbohydrate (300×0.54=162 grams). The percent cook of the Test Diet was shown to be about 80%, with the remaining 20% being uncooked, resistant starch. The percent cook of the Control Diet was shown to be about 90%, with the remaining 10% being uncooked, resistant starch. Accordingly, the cooked proportions of the Test Diet and the Control Diet were approximately 0.8 and 0.9, respectively. This leaves the proportions of resistant starch in the Test and the Control Diets to be approximately 0.2 and 0.1, respectively. Therefore, a dog on the Test Diet who consumed 162 grams of total carbohydrate will consume about 32 grams of resistant starch (162×0.2=32.4 grams), while a dog on Control Diet consumes half the amount of resistant starch per day (162×0.1=16 grams).

What is claimed is:

1. An extruded pet food composition comprising resistant starch in an amount of about 7% to about 30%, by weight based on the total weight of the extruded pet food composition, wherein the extruded pet food composition is a kibble, and wherein a source of the resistance starch is at least one of whole corn and brewers rice.

2. The extruded pet food composition according to claim 1, wherein the extruded pet food composition is a dog food.

3. The extruded pet food composition according to claim 1, wherein the amount of the resistant starch is from about 20% to about 30%, by weight based on the total weight of the extruded pet food composition.

4. The extruded pet food composition of claim 1 made by a method comprising:
   providing pet food raw materials for extrusion; and
   extruding the pet food raw materials using an extrusion device;
   wherein the sum of the specific mechanical energy and the specific thermal energy of the extrusion device is less than 60 W·h/kg,
   wherein the ratio of specific mechanical energy to specific thermal energy is less than 0.5.

5. The pet food composition according to claim 4, wherein the amount of the resistant starch is from about 9% to about 13%, by weight based on the total weight of the pet food composition.

6. The pet food composition according to claim 4, wherein the pet food composition is a dog food.

7. A method of increasing the proportion of at least one of *Lactobacillus* and *Bifidobacterium* in the gastrointestinal tract of an animal comprising:
   administering the pet food composition of claim 4 to the animal; and
   wherein the animal consumes at least about 2.5 g of the resistant starch per kg of animal per day.

8. The method according to claim 7, further comprising decreasing the proportion of *Megamonas* in the gastrointestinal tract of the animal.

9. The method according to claim 7, wherein the animal is a senior animal.

10. A method of making a pet food composition using an extrusion device comprising:
    providing pet food raw materials for extrusion; and
    extruding the pet food raw materials using the extrusion device;
    wherein a specific mechanical energy of the extrusion device is less than about 25 W·h/kg,
    wherein a specific thermal energy of the extrusion device is greater than the specific mechanical energy of the extrusion, and
    wherein the extruded pet food composition comprises resistant starch in an amount of about 7% to about 30% by weight based on the total weight of the pet food composition.

11. The method according to claim 10, wherein the specific thermal energy of the extrusion device is about four times greater than the specific mechanical energy of the extrusion device.

12. The extruded pet food composition of claim 1, wherein the source of the resistant starch is whole corn and brewers rice.

13. The extruded pet food composition of claim 12, wherein a weight ratio of brewers rice to whole corn is about 1:5.

14. The extruded pet food composition of claim 13, wherein the source of resistant starch consists of brewers rice and whole corn.

* * * * *